United States Patent
Schachinger

(10) Patent No.: US 9,927,296 B2
(45) Date of Patent: Mar. 27, 2018

(54) ALIGNMENT SYSTEM FOR LASER SPECTROSCOPY

(71) Applicant: Rosemount Analytical Inc., Houston, TX (US)

(72) Inventor: Peter Schachinger, Billdal (SE)

(73) Assignee: Rosemount Analytical Inc., Houston, TX (US)

( * ) Notice: Subject to any disclaimer, the term of this patent is extended or adjusted under 35 U.S.C. 154(b) by 0 days.

(21) Appl. No.: 14/307,975

(22) Filed: Jun. 18, 2014

(65) Prior Publication Data

US 2014/0375989 A1     Dec. 25, 2014

Related U.S. Application Data

(60) Provisional application No. 61/837,379, filed on Jun. 20, 2013.

(51) Int. Cl.
| | |
|---|---|
| *G01N 21/00* | (2006.01) |
| *G01J 3/02* | (2006.01) |
| *G01J 3/28* | (2006.01) |
| *G01N 21/15* | (2006.01) |
| *G02B 7/182* | (2006.01) |
| *G01N 21/39* | (2006.01) |

(52) U.S. Cl.
CPC .......... *G01J 3/0202* (2013.01); *G01J 3/0289* (2013.01); *G01J 3/28* (2013.01); *G01N 21/15* (2013.01); *G02B 7/1824* (2013.01); *G02B 7/1825* (2013.01); *G01N 21/39* (2013.01)

(58) Field of Classification Search
USPC ................. 372/55, 57, 61–65, 99, 101, 107; 356/300, 399; 359/871; 362/418
See application file for complete search history.

(56) References Cited

U.S. PATENT DOCUMENTS

| | | | |
|---|---|---|---|
| 4,088,396 | A | 5/1978 | Edelstein |
| 4,622,465 | A | 11/1986 | Harig et al. |
| 6,804,284 | B1 | 10/2004 | Kodeda et al. |
| 7,864,323 | B2 | 1/2011 | Kluczynski et al. |

(Continued)

FOREIGN PATENT DOCUMENTS

| | | |
|---|---|---|
| EP | 2479555 A1 | 7/2012 |
| GB | 2313472 A | 11/1997 |

OTHER PUBLICATIONS

Search Report and Written Opinion from International Application No. PCT/US2014/043163, date of filing: Jun. 19, 2014, date of mailing: Oct. 27, 2014. 13 pages.

(Continued)

*Primary Examiner* — Tri T Ton
(74) *Attorney, Agent, or Firm* — Christopher R. Christenson; Kelly, Holt & Christenson, PLLC

(57) ABSTRACT

An adjustable mount for an optical device in a laser spectroscopy system is provided. The adjustable mount includes body configured to mount to a process and a reflector mount having a feature configured to mount an optical device. An interface between the body and the reflector mount allows relative motion between the reflector mount and the body. At least one alignment device is configured to engage the reflector mount and the body to fix a position of the reflector mount relative to the body. An optical device is removably mounted to the reflector mount independent of the alignment device and is sealed to the reflector mount.

14 Claims, 5 Drawing Sheets

(56) References Cited

U.S. PATENT DOCUMENTS

2007/0216984 A1   9/2007   Zheng et al.

OTHER PUBLICATIONS

Supplementary European Search Report for EP Patent Application No. 14813671.6, dated Jan. 19, 2017, 9 pages.
Second Office Action for Chinese Patent Application No. 201480003887.8, dated Jul. 2, 2015, 14 pages including English translation.

US 9,927,296 B2

ALIGNMENT SYSTEM FOR LASER SPECTROSCOPY

CROSS-REFERENCE TO RELATED APPLICATION

The present application is based on and claims the benefit of U.S. Provisional Patent Application Ser. No. 61/837,379, filed Jun. 20, 2013, the content of which is hereby incorporated in its entirety.

BACKGROUND

Gas absorption spectroscopy generally measures the presence and/or concentration of a species of interest in a gas sample by passing a light beam through the sample and detecting the absorption at wavelengths of a particular spectral absorption feature of the species of interest. Generally, such a feature is an absorption line that represents the frequency of light corresponding to vibrational, rotational or electronic transitions of molecules of the gas of interest. Tunable diode lasers provide many advantages for such gas absorption spectroscopy measurements in that the lasers can be tuned to the center of a spectral feature and generate a narrow signal relative to the width of the spectral feature.

Laser absorption spectroscopy can thus offer high speed and relatively high precision capabilities for detecting a variety of trace gas species in gas samples at atmospheric pressures with relatively low cross sensitivity to other gas species or components. Tunable diode laser spectrometers are particularly suited to high sensitivity studies, in part, because they may be frequency-modulated to reduce low frequency laser noise and electronic noise. In general, a laser spectrometer will include a frequency tunable laser that generates an illumination output beam which is directed through a sample cell that contains a gas sample. The output beam is then directed to an optical detector and the signal of the optical detector is demodulated to obtain an absorption induced signal. This absorption induced signal can be used to identify one or more species of interest within the gas sample.

SUMMARY

An adjustable mount for an optical device in a laser spectroscopy system is provided. The adjustable mount includes body configured to mount to a process and a reflector mount having a feature configured to mount an optical device. An interface between the body and the reflector mount allows relative motion between the reflector mount and the body. At least one alignment device is configured to engage the reflector mount and the body to fix a position of the reflector mount relative to the body. An optical device is removably mounted to the reflector mount independent of the alignment device and is sealed to the reflector mount.

DETAILED DESCRIPTION OF THE ILLUSTRATIVE EMBODIMENTS

In spectroscopic detection, the presence of specific substances in fluid such as a gas or liquid is sometimes detected or measured by using a light source and one or more mirrors. The mirrors are generally used to control the path of the light from the source, such as a laser to a detector. Alignment mechanisms are often required to ensure accurate and correct positioning of the mirrors such that the light is properly routed through a measurement cell to a detector. One example of detection where alignment mechanisms are generally used is spectroscopic detection using laser and detector sources, e.g. tunable diode laser absorption spectroscopy.

Being exposed to the chemical processes during the detection process, the mirrors often require cleaning on a regular basis. The cleaning process of such mirrors can be tedious, sometimes requiring special tools and usually requiring realignment of the mirrors after the cleaning process is complete.

Another challenge is created by the mirrors being used in analyzers that are part of containers containing fluids, for example pressurized gas pipes, combustion or chemical processes. In such instances, it is important to keep the process fluid system tightly sealed despite using moving parts in the mirror alignment mechanism. These containers and conduits for which detection may be provided can include sample tubes for extractive measurements or process pipes with in-situ measurements across the pipe. In such containers, contamination prevention requires regular cleaning on the process side.

There is a need for a mechanism in a spectroscopic measurement or detection cell that allows cleaning of the mirror(s) in the analyzer while maintaining a tight seal throughout the cleaning process. Moreover, such cleaning should not require specialized tools nor require realignment (of the mirrors) after each cleaning process.

Figure 1:
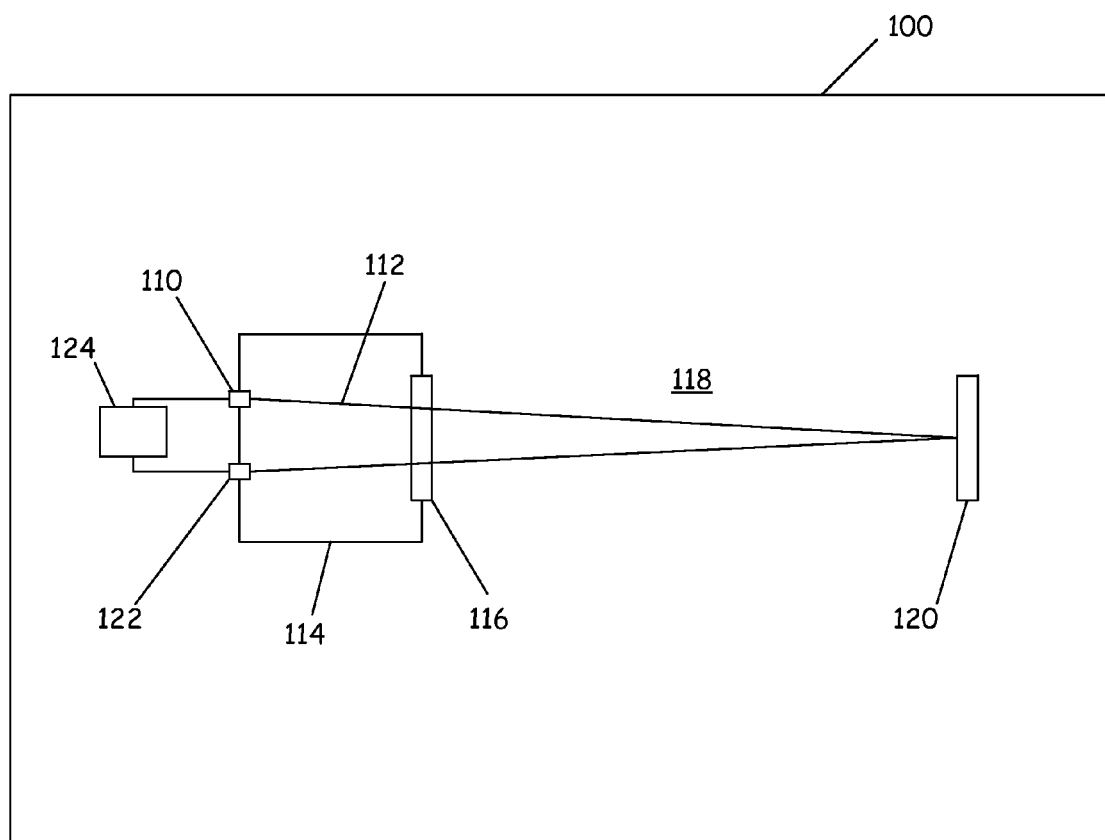
FIG. 1 is a diagrammatic view of a laser spectroscopy system in accordance with an embodiment of the present invention.

FIG. 1 shows one example of a laser spectroscopy system 100 with which aspects of the present invention are particularly useful. Laser spectroscopy system 100 includes laser 110 that generates laser illumination 112. The emitted light 112 passes through a reference cell 114 and through a window 116 and through a process area 118 where it reflects off reflective surface 120. After light 112 reflects from reflective surface 120, it travels back through process area 118, window 116 and reference cell 114 where it is received by the detector 122. Evaluator 124 is coupled to detector 122 such that the received light can be detected or otherwise measured. In order to determine the concentration of the gas in the process area 118, the frequency of emitted light 112 has to be precise and known.

Evaluator 124, in addition to receiving and responding to user input, can control the wavelength of illumination 112 emitted from laser 110. Laser 110 can be a tunable diode laser that generates the emitted illumination 112 at a set wavelength that is determined either by user input or evaluator 124.

In one example, reference cell 114 that the emitted light 112 passes through contains a known concentration of a fluid with a known absorption value. Process area 118, in one embodiment, is a sample cell. However, in other implementation, the process area could also be disposed in situ, by means of a perforated sample cell exposed to the process. Process area 118 contains a sample of a fluid to be tested. For example, in one implementation process area 118 contains a gas of unknown concentration that will be determined by the laser spectroscopy system 100. Reflective surface 120, in one example, is coupled to an optical alignment system.

Reflective surface 120 is in contact with process area 118 during operation, for example, in one embodiment while a process gas is flowing through process area 118. Because of this direct contact, reflective surface 120 will require periodic removal and cleaning. However, as shown in FIG. 1, reflective surface 120 must be properly aligned in order to ensure proper functioning of system 100. Specifically, the emitted light 112 from laser 110 must strike reflective surface 120 such that light 112 bounces back to detector 122. Cleaning reflective surface 120 requires that a mirror, for example, be removed from the system, cleaned, put back in the system and realigned. This removal and realignment process often requires a special set of tools for removal and realignment. It is thus desirable to have a system where reflective surface 120 is easily removable, such that is can be cleaned and replaced without the need of realignment or special tools.

Figure 2A:
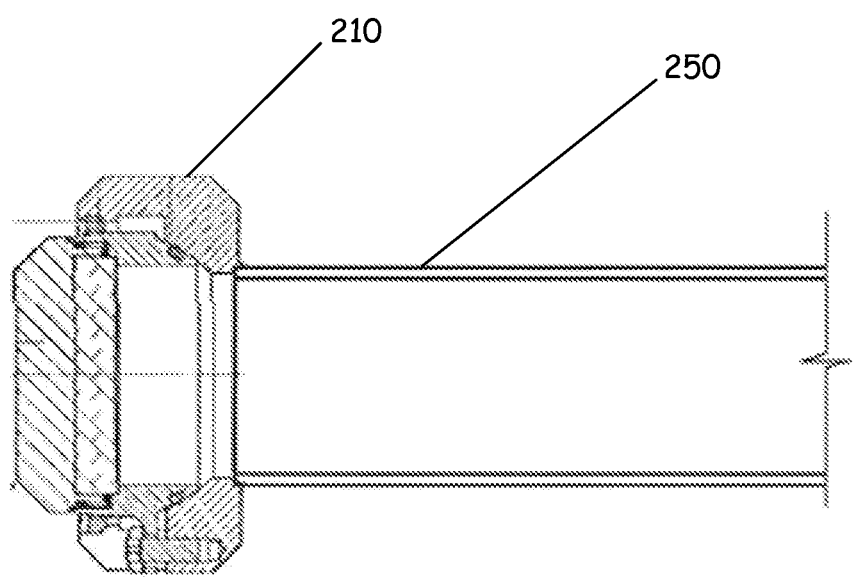
FIG. 2A is a diagrammatic view of an alignment mechanism mounted on a sample tube in accordance with an embodiment of the present invention.
Figure 2B:
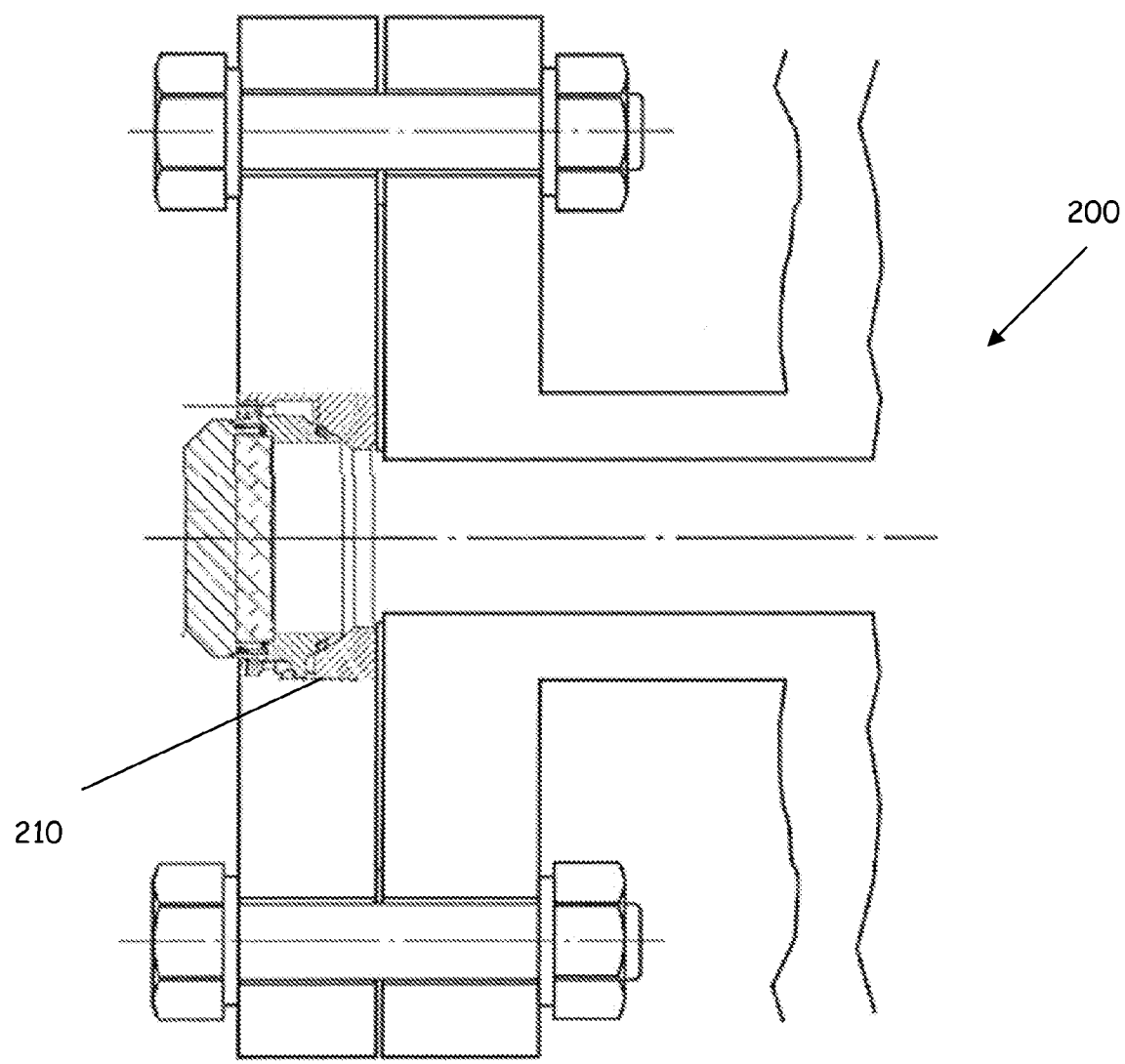
FIG. 2B is a diagrammatic view of an alignment mechanism mounted within a process flow environment in accordance with an embodiment of the present invention.

FIGS. 2A and 2B illustrate an optical alignment mechanism 210 in accordance with embodiments of the present invention. In particular, FIG. 2A shows alignment mechanism coupled to sample tube 250, while FIG. 2B shows alignment mechanism disposed within process system 200. The components of the alignment mechanism 210 are described in further detail with respect to FIGS. 3 and 4. The alignment mechanism 210, as shown in FIGS. 2A and 2B, is also attachable to a variety of other devices by any suitable techniques including welding, for example.

Figure 3:
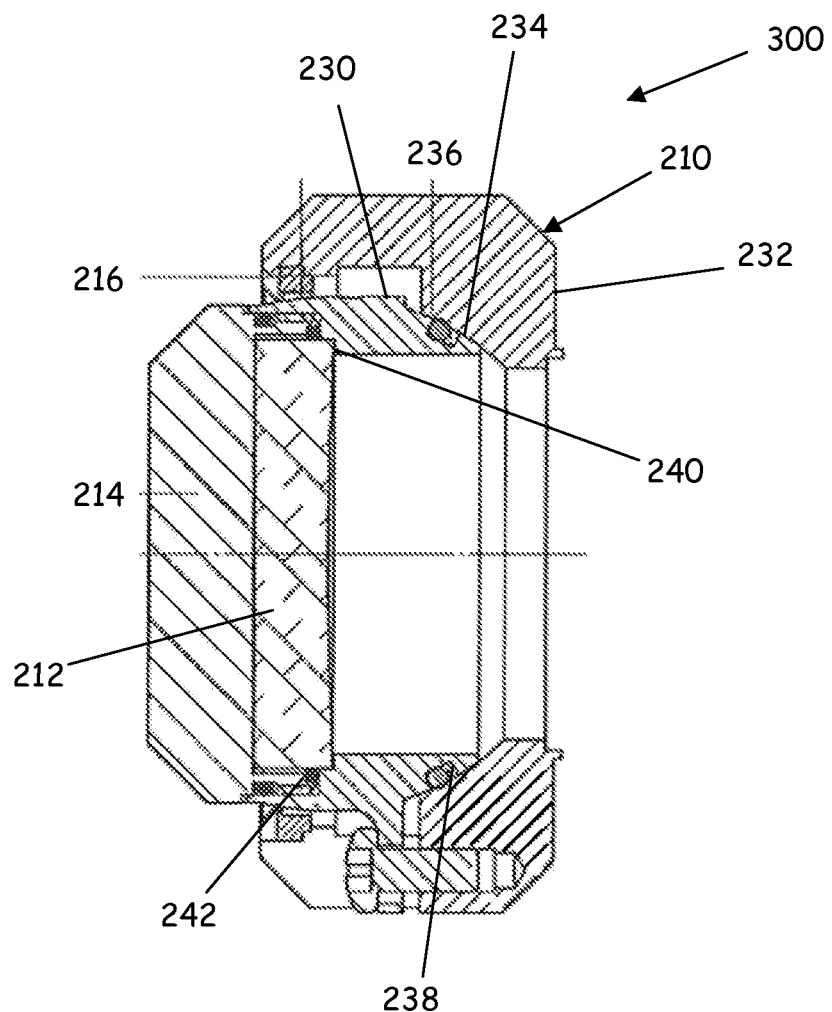
FIG. 3 is a side view of an alignment mechanism in accordance with an embodiment of the present invention.

FIG. 3 is a diagrammatic view of alignment mechanism 210 as part of a reflective surface housing 300. Reflective surface housing 300 consists of alignment mechanism 210 and a reflective surface, for example, in one embodiment, mirror 212. Alignment mechanism 210 includes a reflector mount 230 that interfaces with body 232 at interface 234. Interface 234 allows the position reflector mount 230 to be adjusted relative to body 232 in at least two degrees of freedom. In the illustrated example, interface 234 is spherical. In one embodiment, a lubricant can be provided at interface 234 to enhance functionality. Interface 234 can also include a seal to ensure that the ambient environment does not leak into process area 118 and affect the measurements provided by system, 100. Moreover, such seal helps ensure that process gas from process area 118 cannot escape into the ambient environment. In the example shown, seal 236 is disposed within a groove 238 in reflector mount 230. Also, the potential leak path between mirror 212 and reflector mount 230 is covered by a seal 242.

Reflector mount 230 includes a shoulder 240, or other suitable structure, to receive and reliably mount mirror 212. Additionally, a gasket or O-ring seal 242 is provided to seal mirror 212 to reflector mount 230. Locking ring 216 is coupled to body 232 and is sized and positioned to engage reflector mount 230. Locking ring 216 is designed to be strong enough to withstand internal forces and to ensure an effective seal within the alignment mechanism 210. As shown in FIG. 3, and further detailed in FIG. 4, mirror 212 is removable without removal or adjustment of locking ring 216 or reflector mount 230.

Figure 4:
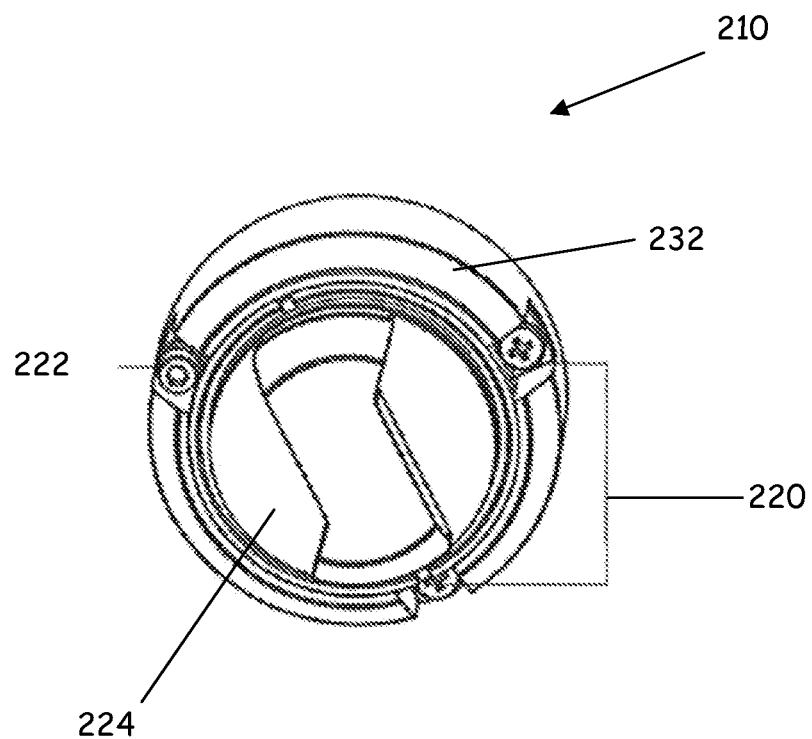
FIG. 4 is an isometric view of an alignment mechanism in accordance with an embodiment of the present invention.

FIG. 4 is an isometric view of an alignment mechanism in accordance with an embodiment of the present invention. Alignment screws 220 are positioned such that they maintain a fixed arrangement between reflector mount 230 and body 232 once the system has been aligned and allow for adjustment of the alignment of the alignment system 210 to fit the requirements of an exemplary system, discussed above with respect to FIG. 1. In the illustrated embodiment, alignment screws 220 are disposed 90 degrees apart such that each screw is responsible for adjusting a different perpendicular angle or axis thereby allowing for a wide range of alignment options to fit different systems. Spring retainer 222 is provided as a counterhold and biases reflector mount 230 against body 232. Lid members 224 allow lid 214 to be easily grasped and opened without using specialized tools.

Alignment mechanism 210 shown in FIGS. 3 and 4 can be mounted to any suitable process or sample device. Once the mechanism is attached to the suitable device, alignment can be accomplished by adjusting screws 220. Thereafter, if replacement or cleaning of the reflector is required, lid 214 can be removed to allow access to the reflector. Once the reflector is replaced, repaired or cleaned, it can be returned to the mount and used without realigning the reflector. Therefore, after a cleaning or replacement has been completed, there is no need to realign the system in order for the reflective surface to properly reflect light, for example, from the laser 110 to the detector 122 as shown in FIG. 1.

The alignment mechanism 210 thus achieves an effective seal towards the process area while also maintaining a consistent alignment that allows for the removal, cleaning and reinsertion of a reflective surface without needing to realign the system. However, as noted in FIG. 4 by alignment screws 220, the alignment is also easily changed as necessary to accomplish moving, for example, the alignment system 210 from a sample tube as shown in FIG. 2A to a process as shown in FIG. 2B. This is all accomplished while maintaining an effective seal that is needed during a chemical process.

Although the present invention has been described with reference to preferred embodiments, workers skilled in the art will recognize that changes may be made in form and detail without departing from the spirit and scope of the invention. For example, while embodiments of the present invention have generally been described with respect to a particular optical component (mirror) disposed in an arrangement wherein alignment is separate from mounting of the optical component, other optical components could be used as well. For example, an optical detector or laser source could be mounted in place of the mirror. Additionally, embodiments of the present invention can be practiced where both the reflective surface and the source/detectors are all mounted such that their alignment is independent of their mounts.

What is claimed is:

1. An adjustable mount for an optical device in a laser spectroscopy system, the adjustable mount comprising:
   a body configured to mount to a process containing a fluid to be tested, the body having a spherical surface;
   a reflector mount having a spherical surface coupled to the spherical surface of the body to define a spherical interface between the body and the reflector mount;

an alignment device coupled to the reflector mount and the body, the alignment device controlling a position of the reflector mount relative to the body; and an optical device removably mounted to the reflector mount independent of the alignment device, the optical device being sealed to the reflector mount and disposed to contact the fluid to be tested; and wherein the body is sealed to the reflector mount at the spherical interface.

2. The adjustable mount of claim 1, wherein the optical device is a mirror.

3. The adjustable mount of claim 1, wherein the optical device is a detector.

4. The adjustable mount of claim 1, wherein the optical device is a tunable laser diode.

5. The adjustable mount of claim 1, and further comprising a seal disposed at the interface.

6. The adjustable mount of claim 1, wherein the lid includes at least one feature configured to allow the lid to be removed by hand.

7. The adjustable mount of claim 5, wherein the at least one alignment device includes a plurality of alignment devices each determining a position of the reflector mount relative to the body in different axis.

8. The adjustable mount of claim 5, wherein the at least one alignment device includes a pair of screws disposed about 90 degrees apart.

9. The adjustable mount of claim 5, and further comprising a spring biasing the reflector mount to the body.

10. The adjustable mount of claim 5, and further comprising a locking ring disposed between the reflector mount and the body and being configured to withstand internal pressures acting against the optical device.

11. The adjustable mount of claim 5, wherein the adjustable mount is attached to an end of an extractive measurement tube.

12. The adjustable mount of claim 5, wherein the adjustable mount is attached to a flange configured to mount to a process.

13. The adjustable mount of claim 5, and further comprising a lubricant disposed at the interface.

14. The adjustable mount of claim 1, and further comprising a lid positioned adjacent the optical device and configured to maintain the optical device within the reflector mount.

* * * * *

UNITED STATES PATENT AND TRADEMARK OFFICE
CERTIFICATE OF CORRECTION

PATENT NO.        : 9,927,296 B2
APPLICATION NO.   : 14/307975
DATED             : March 27, 2018
INVENTOR(S)       : Peter Schachinger Page 1 of 1

It is certified that error appears in the above-identified patent and that said Letters Patent is hereby corrected as shown below:

In the Claims

Column 5, Line 20 through Column 6, Line 17, Claims 7-13 "claim 5" should read "claim 1"

Signed and Sealed this
Fifth Day of June, 2018

Andrei Iancu
*Director of the United States Patent and Trademark Office*